US006419879B1

United States Patent
Cooper et al.

(10) Patent No.: US 6,419,879 B1
(45) Date of Patent: Jul. 16, 2002

(54) COMPOSITION AND METHOD FOR CONTROLLING BIOLOGICAL GROWTH USING STABILIZED SODIUM HYPOBROMITE IN SYNERGISTIC COMBINATIONS

(75) Inventors: Andrew J. Cooper, Oswego; Anthony W. Dallmier, Aurora; Robert F. Kelly, Oswego; William F. McCoy, Naperville, all of IL (US); Xi Ma, Singapore (SG)

(73) Assignee: Nalco Chemical Company, Napervilee, IL (US)

( * ) Notice: Subject to any disclaimer, the term of this patent is extended or adjusted under 35 U.S.C. 154(b) by 0 days.

(21) Appl. No.: 09/373,288

(22) Filed: Aug. 12, 1999

Related U.S. Application Data

(60) Continuation-in-part of application No. 09/256,978, filed on Feb. 24, 1999, now Pat. No. 6,322,749, which is a division of application No. 08/963,397, filed on Nov. 3, 1997, now Pat. No. 5,922,745.

(51) Int. Cl.[7] .................................................. C02F 1/50
(52) U.S. Cl. ............................. 422/14; 422/37; 424/723
(58) Field of Search .................. 422/7, 14, 15, 422/16, 37, 17; 424/405, 723

(56) References Cited

U.S. PATENT DOCUMENTS

| | | |
|---|---|---|
| 4,295,932 A | 10/1981 | Pocius |
| 4,427,435 A | 1/1984 | Lorenz et al. |
| 4,539,071 A | 9/1985 | Clifford et al. |
| 4,595,691 A | 6/1986 | LaMarre et al. |
| 4,661,503 A | 4/1987 | Martin et al. |
| 4,906,651 A | 3/1990 | Hsu |
| 5,417,987 A * | 5/1995 | Dietz et al. |
| 5,922,745 A * | 7/1999 | McCarthy et al. |

FOREIGN PATENT DOCUMENTS

| | | |
|---|---|---|
| WO | WO 96/14092 | 5/1996 |
| WO | WO 97/34827 | 9/1997 |

OTHER PUBLICATIONS

Doherty, Francis G. et al. Abstract of "Control of the freshwater fouling bivalve Corbicula fluminea by halogenation", Arch. Environ. Contam. Toxicol. (1986), 15(5), pp. 535–542.*

"Mixtures of Quaternary Ammonium Compounds and Long–Chain Fatty Acids as Antifungal Agents", Applied Microbiology, F.C. Kull, P.C. Eisman, H.D. Sylwestrowicz, R.L. Mayer,9:538–541 (1961).

"Threshold Levels for Bromate Formation in Drinking Water", Water Supply, vol. 13, No. 1, Paris, pp. 157–167, 1995.

"Toxicity and Risk Assessment of Bromate", Water Supply, vol. 13, No. 1, Paris, pp. 29–33, 1995.

* cited by examiner

*Primary Examiner*—Elizabeth McKane
(74) *Attorney, Agent, or Firm*—Kelly L. Cummings; Thomas M. Breininger

(57) ABSTRACT

A synergistic composition and method for controlling biological growth in industrial fluids are disclosed, wherein the composition comprises stabilized sodium hypobromite and at least one compound selected from the group consisting of coco alkyldimethylamine oxide, n-coco alkyltrimethylenediamine, tetra-alkyl phosphonium chloride, 7-oxabicyclo[2.2.1]heptane-2,3-dicarboxylic acid and 4,5-dichloro-2-n-octyl-4-isothiazoline-3-one.

17 Claims, No Drawings

COMPOSITION AND METHOD FOR CONTROLLING BIOLOGICAL GROWTH USING STABILIZED SODIUM HYPOBROMITE IN SYNERGISTIC COMBINATIONS

REFERENCE TO RELATED PATENT

This application is a continuation-in-part of U.S. Ser. No. 09/256,978, filed on Feb. 24, 1999, now U.S. Pat. No. 6,332,749, which is a divisional of U.S. Ser. No. 08/963,397, filed on Nov. 3, 1997, now U.S. Pat. No. 5,922,745.

FIELD OF THE INVENTION

This invention relates generally to biocides and, more particularly, to a composition and method for controlling biological growth using stabilized sodium hypobromite in synergistic combinations.

BACKGROUND OF THE INVENTION

The proliferation of microorganisms and the resultant formation of slime is a problem which commonly occurs in aqueous systems. Problematic slime producing microbes may include bacteria, fungi and algae. Slime deposits typically occur in many industrial aqueous systems including cooling water systems, pulp and paper mill systems, petroleum operations, clay and pigment slurries, recreational water systems, air washer systems, decorative fountains, food, beverage, and industrial process pasteurizers, sweetwater systems, gas scrubber systems, latex systems, industrial lubricants, cutting fluids, etc.

The proliferation of organisms such as mussels and clams is also a problem which occurs in many water systems. Growth of these organisms is a serious problem in municipal and industrial water systems such as once-through or recirculating cooling water systems, cooling ponds, intake pipes, ballast water tanks and ship reservoirs that draw water from infested bodies of water.

Biocides and antimicrobials are used to control microbial growth in a number of different aqueous media. As used herein, "control" is defined to include both inhibition and removal. If left untreated, microbes and microbial biofilms (slimes) can cause deterioration of cooling tower structures, loss in heat exchange efficiency in a cooling system, aesthetic defects in decorative fountains, promotion and acceleration of corrosion on metal surfaces, increased down time, or breaks in paper sheets in pulp and paper systems. Bacterial slimes may also be objectionable as they relate to cleanliness and sanitation in breweries, dairies, and other industrial food and beverage process water systems. The proliferation of microbial contamination in lubricants and cutting fluids is a common problem due to the elevated temperatures and unsanitary conditions found in many metal working plants.

For many types of municipal and industrial water systems, screening of intake water is often performed to prevent the entrance of large objects, including mature clams and mussels. This screening, however, does not prevent the passage of juvenile macroinvertebrates. These early life stages of the macroinvertebrates attach within water systems and mature to a size and density which cause fouling. This growth can cause severe plugging and damage to the systems they colonize, resulting in system down time and costly cleanings and repairs. As a consequence of the deleterious effects of uncontrolled biological growth and contamination in many industrial processes, different biocides and antimicrobials have been developed to aid in eliminating and controlling biological growth.

Often, one biocide is insufficient to control biological growth in the aqueous media. Biocides may act in combination, i.e. synergistically, to yield better biocidal performance as opposed to the efficacy obtained when each biocide is used separately. Biocides may act on the target organism in a number of different ways to cause cell stress or death. The mechanisms by which biocides exert biocidal activity depend upon a number of factors which include the chemical properties of the biocide, and the biochemical and physical characteristics of the target organism. Some biocides target the cell membrane or cell wall. Others target critical enzymes or the cellular metabolic machinery which leads to cell death or disruption of cellular replication.

The combination of two biocides may yield enhanced efficacy beyond the cumulative or additive effect of the two biocides. This likely reflects a synergistic biocidal effect on some essential component(s) of the cell for survival and sustained growth. A combination of two biocides that are synergistic allows for the addition of lesser amounts of the individual biocides to achieve the desired level of control. This has both advantageous environmental and economic impacts. It allows for reduced discharge of potential environmental pollutants and a more cost effective control program for diverse industrial systems.

It is an object of the present invention to provide novel biocidal compositions which provide enhanced effectiveness for controlling the growth of both microorganisms and macroorganisms in industrial fluids. It is another object of this invention to provide an improved method for controlling microorganisms and macroorganisms in industrial fluids. It is an advantage of the present invention that the biocidal compositions permit a reduction in the amount of biocide required to achieve acceptable biological control.

Important applications of the synergistic biocidal compositions of the present invention include, but are not limited to, controlling the growth of microorganisms such as bacteria, fungi and algae, and macroorganisms such as zebra mussels, blue mussels and the Asiatic clam in aqueous media. The composition of the present invention possesses unexpected synergistic activity against microorganisms and macroorganisms.

Stabilized sodium hypobromite is less volatile and more stable than other halogenated molecules such as sodium hypochlorite and sodium hypobromite. Also, much higher levels of available halogen for microbial disinfection are attained using stabilized sodium hypobromite than with other halogenated antimicrobials. Further, stabilized sodium hypobromite yielded reduced generation of adsorbable organic halogen (AOX) in laboratory studies and process waters.

This invention provides superior biological control by combining stabilized sodium hypobromite with at least one compound selected from the group consisting of coco alkyldimethylamine oxide, n-coco alkyltrimethylenediamine, tetra-alkyl phosphonium chloride, 7-oxabicyclo[2.2.1]heptane-2,3-dicarboxylic acid and 4,5-dichloro-2-n-octyl-4-isothiazoline-3-one. The combination of the two biocides leads to unexpectedly superior results, and allows for significantly less use of either biocide compared to the necessary amount of each individual biocide to achieve the same biocidal performance. In addition to biocidal synergism, the use of these biocide combinations may result in improved removal of adherent biomass due to the biocidal persistence of coco alkyldimethylamine oxide, n-coco alkyltrimethylenediamine, tetra-alkyl phosphonium chloride, 7-oxabicyclo[2.2.1]heptane-2,3-dicarboxylic acid and 4,5-dichloro-2-n-octyl-4-isothiazoline-3-one coupled with the reactivity and biofilm removal properties of stabilized sodium hypobromite. As is well known in the art, stabilized sodium hypobromite, coco alkyldimethylamine oxide, n-coco alkyltrimethylenediamine, tetra-alkyl phosphonium chloride, 7-oxabicyclo[2.2.1]heptane-2,3-dicarboxylic acid and 4,5-dichloro-2-n-octyl-4-isothiazoline-3-one exhibit biocidal activity when used alone. However, the prior art does not teach or suggest the performance advantages of the inventive combinations or the resulting synergistic behavior.

SUMMARY OF THE INVENTION

The composition of the present invention comprises stabilized sodium hypobromite and at least one compound selected from the group consisting of coco alkyldimethylamine oxide, n-coco alkyltrimethylenediamine, tetra-alkyl phosphonium chloride, 7-oxabicyclo[2.2.1]heptane-2,3-dicarboxylic acid and 4,5-dichloro-2-n-octyl-4-isothiazoline-3-one.

The inventive composition effectively controls biological growth in industrial fluids.

DETAILED DESCRIPTION OF THE INVENTION

The present invention is directed to a composition and method for controlling biological growth in industrial fluids using stabilized sodium hypobromite in synergistic combinations. In accordance with this invention, stabilized sodium hypobromite is added to the industrial fluid in combination with another compound. Suitable compounds which may be used in combination with the stabilized sodium hypobromite include, but are not limited to, surfactants such as coco alkyldimethylamine oxide and n-coco alkyltrimethylenediamine, and non-oxidizing biocides such as tetra-alkyl phosphonium chloride, 7-oxabicyclo[2.2.1] heptane-2,3-dicarboxylic acid (also known as endothall) and 4,5-dichloro-2-n-octyl-4-isothiazolin-3-one.

The biological growth may be microbiological or macrobiological in nature. Microbiological growth includes bacteria, fungi, algae and combinations thereof. Macrobiological growth includes zebra mussels (*Dreissena polymorpha, Dreissena bugensis*), blue mussels (*Mytilus edulis*), and the Asiatic clam (*Corbicula fluminea*).

The stabilized sodium hypobromite may be sodium hypobromite stabilized with sodium sulfamate. The sodium hypobromite may be stabilized with an alkali metal sulfamate, such as sodium sulfamate. Moreover, the sodium hypobromite may also be stabilized with an acid amide derivative selected from the group consisting of carbonic acids, hydrogen cyanide, carboxylic acids, amino acids, sulfuric acids, phosphoric acids and boric acids.

The industrial fluids include cooling waters; food, beverage and industrial process waters; pulp and paper mill systems; brewery pasteurizers; sweetwater systems; air washer systems; oil field drilling fluids and muds; petroleum recovery processes; industrial lubricants; cutting fluids; heat transfer systems; gas scrubber systems; latex systems; clay and pigment systems; decorative fountains; water intake pipes; ballast water tanks and ship reservoirs, among others.

The amount of stabilized sodium hypobromite may range from about 0.05 ppm to about 1000 ppm total residual oxidant (as chlorine) and the amount of the compound selected from the group consisting of coco alkyldimethylamine oxide, n-coco alkyltrimethylenediamine, tetra-alkyl phosphonium chloride, 7-oxabicyclo [2.2.1]heptane-2,3-dicarboxylic acid and 4,5-dichloro-2-n-octyl-4-isothiazoline-3-one ranges from about 0.05 ppm to about 1000 ppm active ingredient (active ingredient refers to the amount of the compound in the industrial fluid). "Total residual oxidant" as used herein is defined as hypobromite or hypobromous acid, expressed as chlorine, including chemical combinations of those two compounds with ammonia or organic nitrogen-containing compounds.

As used herein, the term "stabilized sodium hypobromite" indicates NaOBr stabilized with sodium sulfamate. However, NaOBr can be stabilized with other stabilizers which includes the acid amide derivatives of carbonic acids, hydrogen cyanide, carboxylic acids, amino acids, sulfuric acids, phosphoric acids and boric acids. Moreover, stabilizers can be selected from the group of compounds having an N—H or $NH_2$ group adjacent to an electron withdrawing functional group such as C=O, S=O, P=O, or B=O.

Stabilization of NaOBr is desirable to prevent disproportionation into halates and halides upon storage. As a result of stabilization, these biocides can be stored more safely since less bromate is generated, fewer organic molecules containing halogens are formed, and volatility is reduced. A stabilized aqueous alkali or alkaline earth metal hypobromite solution may be prepared in the following fashion:

a. Mixing an aqueous solution of alkali or alkaline earth metal hypochlorite having from about 5 percent to about 70 percent available halogen as chlorine with a water soluble bromide ion source;

b. Allowing the bromide ion source and the alkali or alkaline earth metal hypochlorite to react to form a 0.5 to 70 percent by weight aqueous solution of unstabilized alkali or alkaline earth metal hypobromite;

c. Adding to the unstabilized solution of alkali or alkaline earth metal hypobromite an aqueous solution of an alkali metal sulfamate in a quantity to provide a molar ratio of alkali metal sulfamate to alkali or alkaline earth metal hypobromite from about 0.5 to about 7; and d. Recovering a stabilized aqueous alkali or alkaline earth metal hypobromite solution.

The stabilized sodium hypobromite utilized herein (STABREX®) is available from Nalco Chemical Company of Naperville, Ill.

The synergistic composition of this invention may be added separately to an industrial fluid or may be formulated as a simple mixture comprising its essential ingredients.

It may be the case that the stabilized sodium hypobromite will act synergistically against microorganisms when combined with other non-oxidizing biocides or surfactants. It is expected that the above detailed description would also apply to a composition and method for controlling macrobiological growth in industrial fluids comprising a combination of stabilized sodium hypobromite with other non-oxidizing biocides. Examples of other non-oxidizing biocides include glutaraldehyde, 2,2-dibromo-3-nitrilopropionamide (DBNPA),2-bromo-2-nitropropane-1,3 diol, 1-bromo-1-(bromomethyl)-1,3-propanedicarbonitrile, tetrachloroisophthalonitrile, alkyldimethylbenzylammonium chloride (ADBAC), dimethyl dialkyl ammonium chloride, poly(oxyethylene(dimethyliminio)ethylene (diemethyliminio)ethylene dichloride, methylene bisthiocyanate (MBT), 2-decylthioethanamine (DTEA), tetrakishydroxymethyl phosphonium sulfate (THPS), dithiocarbamate, cyanodithioimidocarbonate, 2-methyl-5- nitroimidazole-1-ethanol, 2-(2-bromo-2-nitroethenyl) furan (BNEF), beta-bromo-beta-nitrostyrene (BNS), beta-nitrostyrene (NS), beta-nitrovinyl furan (NVF), 2-bromo-2-bromomethyl-glutaronitrile (BBMGN), bis(trichloromethyl) sulfone, S-(2-hydroxypropyl)thiomethanesulfonate, tetrahydro-3,5-dimethyl-2H-1,3,5-hydrazine-2-thione, 2-(thiocyanomethylthio)benzothiazole (TCTMB), 2-bromo-4'-hydroxyacetophenone, 1,4-bis(bromoacetoxy)-2-butene, bis(tributyltin)oxide (TBTO), copper sulfate, 2-(tert-butylamino)-4-chloro-6-(ethylamino)-s-triazine, dodecylguanidine acetate and dodecylguanadine hydrochloride (DGH).

EXAMPLES

The following examples are intended to be illustrative of the present invention and to teach one of ordinary skill how to make and use the invention. These examples are not intended to limit the invention or its protection in any way.

Synergism was determined in each of the Examples below by an industrially accepted method as described by Kull, F. C., Eisman, P. C., Sylwestrowicz, H. D. and Mayer, R. L. in *Applied Microbiology*, 9:538–541 (1961), using the equation for the calculation of a synergy index determined by:

$$Q_a/Q_A + Q_b/Q_B = \text{Synergy Index (S.I.)}$$

wherein $Q_A$=concentration of compound A in parts per million (ppm) acting alone, which produced an endpoint;

$Q_a$=concentration of compound A in ppm, in the mixture, which produced an endpoint;

$Q_B$=concentration of compound B in ppm acting alone which produced an endpoint;

$Q_b$=concentration of compound B in ppm, in the mixture, which produced an endpoint.

When the sum of $Q_a/Q_A$ and $Q_b/Q_B$ is greater than 1.0, antagonism is indicated. When the sum is equal to 1.0, additivity is indicated, and when the sum is less than 1.0, synergy is demonstrated.

Example 1

*Chlorella sorokiniana* green algae were grown in Proteose medium for three weeks, harvested by centrifugation, and resuspended in synthetic cooling water (pH 8.2). For the assay, 96-well tissue culture microplate (FALCON® 3075) wells were prepared with 200 μL of the indicated biocides in synthetic cooling water. 100 μL of a *Chlorella sorokiniana*-cell suspension [$10^7$ Colony Forming Units (CFU) per mL] were inoculated into each microplate well providing a 300 μL total volume. Microplates were covered with the provided lid and incubated at 25° C. for six days with 16 hour/8 hour light/dark cycles (cool-white fluorescent lamps, 1255 lux). Following incubation, the supernatant from each microplate well was removed by aspiration and chlorophyll was extracted from the remaining cells using dimethylsulfoxide (DMSO). The reduction in algae cell chlorophyll content due to algicidal activity was measured using the optical density at 650 nm (Beckman Biomek® plate reader) of each extraction. As shown below in Table 1, synergy was indicated.

TABLE 1

| Biocide | Biocide Amount (ppm) | Optical Density ($OD_{650nm}$) | Synergy Index[1] |
|---|---|---|---|
| None | None | 0.412 | |
| A | 16 | 0.097 | |
| A | 8 | 0.293 | |
| A | 4 | 0.356 | |
| A | 2 | 0.373 | |
| A | 1 | 0.396 | |
| A | 0.5 | 0.412 | |
| A | 0.25 | 0.390 | |
| B | 16 | 0.057 | |
| B | 8 | 0.085 | |
| B | 4 | 0.192 | |
| B | 2 | 0.196 | |
| B | 1 | 0.251 | |
| B | 0.5 | 0.279 | |
| B | 0.25 | 0.369 | |
| A/B | 8/0.5 | 0.122 | 0.750 |
| A/B | 1/1 | 0.216 | 0.563 |
| A/B | 0.5/1 | 0.243 | 0.531 |
| A/B | 0.25/1 | 0.210 | 0.516 |

A = STABREX ® stabilized sodium hypobromite, available from Nalco Chemical Company, Naperville, IL. Biocide measured as ppm total residual oxidant.
B = 4,5-dichloro-2-n-octyl-4-isothiazolin-3-one, available from Rohm and Haas Company, Philadelphia, PA. Biocide measured as ppm active ingredient.
[1]Endpoint used for synergism index calculations was $OD_{650}$ = 0.250.

Example 2

The test protocol described above in Example 1 was utilized. However, for this example, the test inoculum was 100 μL of *Scenedesmus obliquus* green algae ($10^6$ CFU/mL). As shown below in Table 2, synergy was indicated.

TABLE 2

| Biocide | Biocide Amount (ppm) | Optical Density ($OD_{650nm}$) | Synergy Index[1] |
|---|---|---|---|
| None | None | 0.164 | |
| A | 32 | 0.051 | |
| A | 16 | 0.095 | |
| A | 8 | 0.108 | |
| A | 4 | 0.134 | |
| A | 2 | 0.161 | |
| A | 1 | 0.149 | |
| A | 0.5 | 0.156 | |
| C | 256 | 0.044 | |
| C | 128 | 0.046 | |
| C | 64 | 0.048 | |
| C | 32 | 0.063 | |
| C | 16 | 0.092 | |
| C | 8 | 0.105 | |
| C | 4 | 0.118 | |
| A/C | 16/4 | 0.071 | 0.625 |
| A/C | 16/8 | 0.066 | 0.750 |
| A/C | 8/8 | 0.075 | 0.500 |
| A/C | 8/16 | 0.066 | 0.750 |
| A/C | 4/16 | 0.063 | 0.625 |

A = STABREX ® stabilized sodium hypobromite, available from Nalco Chemical Company, Naperville, IL. Biocide measured as ppm total residual oxidant.
C = Coco alkyldimethylamine oxide measured as ppm active ingredient.
[1]Endpoint used for synergism index calculations was $OD_{650}$ = 0.080.

Example 3

Green algae isolated from a Malaysian cooling tower were grown in Bold's Basal Medium for several days, harvested by centrifugation, and resuspended in synthetic cooling water (pH 8.2). For the assay, 12-well tissue culture microplate (FALCON®) wells were prepared with 4 mL algae suspension ($OD_{664nm}$=0.15) and dosed with the indicated biocide. Plates were incubated at 25° C. for 24 hours with continuous illumination. Following incubation, a 1 mL sample from each microplate well was removed and chlorophyll in each sample was measured using extraction with 90% acetone and a standard trichromatic spectrophotometric procedure [Standard Methods for the Examination of Water and Wastewater, $19^{th}$ edition (1995)]. The results are shown below in Table 3 and are reported as percent reduction in chlorophyll relative to an untreated control culture. Synergy was indicated.

TABLE 3

| Biocide | Biocide Amount (ppm) | Percent Reduction in Chlorophyll | Synergy Index[1] |
|---|---|---|---|
| None | None | 0 | |
| A | 32 | 68.74 | |
| A | 16 | 34.12 | |
| A | 8 | 26.98 | |
| A | 4 | 0 | |
| A | 2 | 0 | |
| A | 1 | 0 | |
| A | 0.5 | 0 | |
| D | 16 | 100 | |
| D | 12 | 86.52 | |
| D | 8 | 66.27 | |
| D | 4 | 37.47 | |
| D | 2 | 19.12 | |
| D | 1 | 7.91 | |
| A/D | 2/2 | 51.20 | 0.310 |
| A/D | 4/2 | 46.61 | 0.380 |
| A/D | 8/2 | 42.83 | 0.500 |
| A/D | 1/4 | 54.94 | 0.530 |
| A/D | 2/4 | 61.82 | 0.560 |
| A/D | 4/4 | 64.54 | 0.630 |

A = STABREX ® stabilized sodium hypobromite, available from Nalco Chemical Company, Naperville, IL. Biocide measured as ppm total residual oxidant.
D = tetra-alkyl phosphonium chloride, available from FMC, Princeton, NJ as Bellacide ® 350. Biocide measured as ppm active ingredient.
[1]Endpoint used for synergism index calculations was chlorophyll reduction ≧40%.

While the present invention is described above in connection with preferred or illustrative embodiments, these embodiments are not intended to be exhaustive or limiting of the invention. Rather, the invention is intended to cover all alternatives, modifications and equivalents included within its spirit and scope, as defined by the appended claims.

What is claimed is:

1. A composition for controlling biological growth in industrial fluids comprising effective amounts of stabilized sodium hypobromite and at least one compound selected from the group consisting of coco alkyldimethylamine oxide, n-coco alkyltrimethylenediamine, tetra-alkyl phosphonium chloride, 7-oxabicyclo[2.2.1]heptane-2,3-dicarboxylic acid and 4,5-dichloro-2-n-octyl-4-isothiazoline-3-one.

2. The composition of claim 1 wherein the biological growth is microbiological growth.

3. The composition of claim 2 wherein the microbiological growth is selected from the group consisting of bacteria, fungi, algae and combinations thereof.

4. The composition of claim 1 wherein the biological growth is macrobiological growth.

5. The composition of claim 4 wherein the macrobiological growth is selected from the group consisting of zebra mussels, blue mussels and the Asiatic clam.

6. The composition of claim 1 wherein the stabilized sodium hypobromite is sodium hypobromite stabilized with sodium sulfamate.

7. The composition of claim 6 wherein the sodium hypobromite is stabilized with an alkali metal sulfamate.

8. The composition of claim 6 wherein the sodium hypobromite is stabilized with an acid amide derivative selected from the group consisting of carbonic acids, hydrogen cyanide, carboxylic acids, amino acids, sulfuric acids, phosphoric acids and boric acids.

9. The composition of claim 1 wherein the industrial fluids are selected from the group consisting of cooling waters; food, beverage and industrial process waters; pulp and paper mill systems; brewery pasteurizers; sweetwater systems; air washer systems; oil field drilling fluids and muds; petroleum recovery processes; industrial lubricants; cutting fluids; heat transfer systems; gas scrubber systems; latex systems; clay and pigment systems; decorative fountains; water intake pipes; ballast water tanks and ship reservoirs.

10. The composition of claim 1 wherein the amount of stabilized sodium hypobromite ranges from about 0.05 ppm to about 1000 ppm total residual oxidant and the amount of the compound selected from the group consisting of coco alkyldimethylamine oxide, n-coco alkyltrimethylenediamine, tetra-alkyl phosphonium chloride, 7-oxabicyclo[2.2.1]heptane-2,3-dicarboxylic acid and 4,5-dichloro-2-n-octyl-4-isothiazoline-3-one ranges from about 0.05 ppm to about 1000 ppm active ingredient.

11. A method of controlling biological growth in an industrial fluid which comprises the step of adding to the industrial fluid effective biological growth controlling amounts of stabilized sodium hypobromite and at least one compound selected from the group consisting of coco alkyldimethylamine oxide, n-coco alkyltrimethylenediamine, tetra-alkyl phosphonium chloride, 7-oxabicyclo[2.2.1]heptane-2,3-dicarboxylic acid and 4,5-dichloro-2-n-octyl-4-isothiazoline-3-one.

12. The method of claim 11 wherein the biological growth is microbiological growth.

13. The method of claim 12 wherein the microbiological growth is selected from the group consisting of bacteria, fungi, algae and combinations thereof.

14. The method of claim 11 wherein the biological growth is macrobiological growth.

15. The method of claim 14 wherein the macrobiological growth is selected from the group consisting of zebra mussels, blue mussels and the Asiatic clam.

16. The method of claim 11 wherein the industrial fluid is selected from the group consisting of cooling waters; food, beverage and industrial process waters; pulp and paper mill systems; brewery pasteurizers; sweetwater systems; air washer systems; oil field drilling fluids and muds; petroleum recovery processes; industrial lubricants; cutting fluids; heat transfer systems; gas scrubber systems; latex systems; clay and pigment systems; decorative fountains; water intake pipes; ballast water tanks and ship reservoirs.

17. The method of claim 11 wherein the amount of stabilized sodium hypobromite ranges from about 0.05 ppm to about 1000 ppm total residual oxidant and the amount of the compound selected from the group consisting of coco alkyldimethylamine oxide, n-coco alkyltrimethylenediamine, tetra-alkyl phosphonium chloride, 7-oxabicyclo[2.2.1]heptane-2,3-dicarboxylic acid and 4,5-dichloro-2-n-octyl-4-isothiazoline-3-one ranges from about 0.05 ppm to about 1000 ppm active ingredient.

* * * * *

UNITED STATES PATENT AND TRADEMARK OFFICE
CERTIFICATE OF CORRECTION

PATENT NO. : 6,419,879 B1
DATED : July 16, 2002
INVENTOR(S) : Andrew J. Cooper, Anthony W. Dallmier, Robert F. Kelly, William F. McCoy and Xi Ma It is certified that error appears in the above-identified patent and that said Letters Patent is hereby corrected as shown below:

<u>Title page,</u>
Item [73], "Assignee: Nalco Chemical Company, Napervilee, IL (US)" should read as -- Assignee: Nalco Chemical Company, Naperville, IL (US) --

Signed and Sealed this

Nineteenth Day of November, 2002

*Attest:*

*Attesting Officer*

JAMES E. ROGAN
*Director of the United States Patent and Trademark Office*